United States Patent [19]

VanDeripe

[11] Patent Number: 5,137,510
[45] Date of Patent: Aug. 11, 1992

[54] SYSTEM AND METHOD FOR OXYGENATION OF THE HEART USING SUBPERICARDIAL FLUIDS

[75] Inventor: Donald R. Van Deripe, Lake St. Louis, Mo.

[73] Assignee: Mallinckrodt Medical, Inc., St. Louis, Mo.

[21] Appl. No.: 684,421

[22] Filed: Apr. 12, 1991

Related U.S. Application Data

[63] Continuation-in-part of Ser. No. 627,178, Dec. 14, 1990.

[51] Int. Cl.$^5$ .............................................. A61M 5/178
[52] U.S. Cl. ........................................ 604/28; 604/49; 604/158
[58] Field of Search ............... 604/27, 28, 96, 158, 604/49, 51, 52, 53; 128/DIG. 12

[56] References Cited

U.S. PATENT DOCUMENTS

| | | | |
|---|---|---|---|
| 4,252,827 | 2/1981 | Yokoyama et al. | 514/776 |
| 4,413,989 | 11/1983 | Schjeldahl et al. | 604/96 |
| 4,448,188 | 5/1984 | Loeb | 604/96 |
| 4,795,423 | 1/1989 | Osterholm | 604/28 |
| 4,799,479 | 1/1989 | Spears | 604/28 |
| 4,902,276 | 2/1990 | Zakko | 604/28 |
| 4,963,130 | 10/1990 | Osterholm | 604/28 |
| 4,981,691 | 1/1991 | Osterholm et al. | 604/28 |

*Primary Examiner*—Gene Mancene
*Assistant Examiner*—Michael Lynch
*Attorney, Agent, or Firm*—David A. Hey

[57] ABSTRACT

The present invention relates to a system and method for oxygenation of ischemic tissue. In particular, the present invention relates to a system and method for supplying oxygen to the myocardium of the heart through means other than the coronary arteries. The system of the present invention comprises a catheter which may be used to infuse preoxygenated carrier solutions, such as perfluorocarbon emulsions, directly into the pericardial space; i.e. the space between the pericardium and the epicardial surface. The preoxygenated solutions may be periodically or continuously withdrawn and fresh solutions then infused into the pericardial space.

39 Claims, No Drawings

SYSTEM AND METHOD FOR OXYGENATION OF THE HEART USING SUBPERICARDIAL FLUIDS

RELATION TO OTHER APPLICATIONS

This application is a continuation-in-part application of U.S. Ser. No. 07/627,178, filed Dec. 14, 1990.

BACKGROUND

The present invention relates to a system and method for oxygenation of ischemic heart tissue. In particular, the present invention relates to a system and method for supplying oxygen to the myocardium of the heart through means other than the coronary arteries.

There are an estimated 1.5 million heart attacks recorded annually in the United States alone; of which only 1.2 million (80%) victims reach the hospital alive. Another 300,000 die in the hospital to account for an annual death rate of approximately 600,000.

The 900,000 heart attack or myocardial infarction (MI) victims which do survive, are affected by a significant morbidity rate caused by irreversible damage to the heart, such as scarring of the myocardial tissue.

In addition to the damage caused by heart attacks, patients which undergo percutaneous transluminal coronary angioplasty (PTCA) are at risk of developing iatrogenic myocardial ischemia. In particular, when PTCA is performed, a dilatation balloon is inflated within a coronary artery, thus blocking blood flow to the distal myocardium during the inflation period. It is often desirable to maintain the balloon in an inflated condition for periods up to two minutes or longer, during which time significant ischemia may develop.

In both clinical situations; i.e. MI and PTCA, there is a great need for a system and method of providing oxygen to the myocardial tissue, until such time as reperfusion of blood can be reestablished. In particular, following an MI, there is always a certain time period of non-perfusion during which ischemia may develop. This is especially true during patient transport to the hospital, and until occluded vessels can be reopened by PTCA or thrombolytic agents, for example.

It is generally thought that ischemia caused by non-perfusion periods of 30 minutes or less, is fully reversible with no permanent damage to the heart muscle. Ischemic periods of 30 to 90 minutes will generally cause myocardial stunning and often the heart fails to completely recover or does so over a relatively long period of time. If non-perfusion occurs for periods beyond 2 to 4 hours, the ischemia which develops will generally result in the death of the unperfused myocardial portions.

In order to keep ischemia to a minimum, typical PTCA procedures employ balloon inflation times of only 30 to 60 seconds. Longer periods of inflation are possible by monitoring the ischemia qualitatively by means such as an electrocardiogram recording. Relatively recent approaches of supplying oxygen to the myocardial tissue during PTCA, include perfusing oxygenated blood or perfluorocarbon emulsions through a central lumen of the PTCA catheter. Such techniques have been reported in several journals including Nunn et al, Am. J. Cardiol., 52:203-205, 1983; Kolodgie et al, Am. Heart J., 112:1192-1201, 1986; Glogar et al, Science, 211:1439-1441, 1981. Further, in cases of PTCA following an MI, intravenous introduction of perfluorocarbons has been used to reoxygenate the myocardium. However, such is possible only when blood flow has already been reestablished through stenosed or thrombus blocked vessels.

The administration of thrombolytic agents either intravenously or directly into the coronary arteries is another means of reopening blocked vessels. Thrombolytic agents work by dissolving the occluding thrombus and thereby reestablishing blood flow. When thrombolytic agents are administered properly, they can be expected to restore blood flow relatively quickly in cases of minor MIs. However, in cases of massive MIs, or in oases of delayed administration, the efficacy of the agents can be drastically reduced. Further, there are several disadvantages associated with the use of thrombolytic agents, such as the selection of proper dose, hemorrhagic side effeots, delayed dissolving action of 30 to 60 minutes or more, short half life in the blood, and expense. In addition, not all patients are suitable candidates for the use of thrombolytic agents based on factors such as age, bleeding conditions, etc.

Delays in reperfusion of the myocardium following an MI give rise to physiological and biochemical changes in the ischemic tissue and in the white blood cells. These changes may trigger the release of oxygen free radicals during the first few minutes following reestablishment of blood flow. The free radicals can add further damage to the already at risk ischemic tissue.

Several drugs have been studied as possible blockers of reperfusion damage to the heart. Many of these have shown effectiveness after intravenous or intracoronary administration. In particular, the administration of perfluorochemical emulsions have been shown to be of potential value in preventing reperfusion damage when used at the time of reperfusion. (See Forman et al, J. Am. Coll. Cardiol., 9:1082-1090, 1987; Roberts et al, Am. J. Cardiol., 57:1202-1205, 1986; Bajaj et al, Circulation, 79:645-656, 1989.) It is believed that this damage prevention arises from the ability of perfluorochemicals to carry oxygen to the tissue, to scavenge any released oxygen radicals, and to flush white blood cells from the reperfused segments.

However, all of the methods and drugs mentioned above, suffer from the same disadvantage that their effectiveness is dependent on the reopening of blocked vessels. In particular, all of the prior art methods are carried out by intravenous or intracoronary administration which necessarily requires the reopening of blocked vessels to deliver the drugs to the at risk myocardium.

Therefore, there is a great need for a system and method which can be used to supply oxygen to the myocardium by means other than through the coronary arteries.

One study examined the administration of dissolved oxygen gas into the pericardial space as means of providing some protection against ischemia produced by ligation of the left anterior descending coronary artery. (See Sedlarik et al, Res. Exp. Med. (Berl), 183:177-181, 1983.) This study also included an experiment wherein oxygen was bubbled into saline. However, saline will not generally provide for adequate oxygenation or removal of carbon dioxide. Efficacy of this method was apparently based on the uptake and transport of oxygen by the lymphatic channels. However, there are risks in such a procedure, such as, the inability of saline solutions to carry sufficient quantities of oxygen, and the inability to remove carbon dioxide thus giving rise to acidosis. In addition, administration of oxygen in saline does not provide for the concurrent administration of therapeutic drugs or nutrients.

Therefore, there is also a great need to provide a system and method of which can be used to supply oxygen to the myocardium by means other than through the coronary arteries and which avoids the limitations of using a gas dissolved in a saline solution.

OBJECTS OF THE INVENTION

It is one object of the present invention to provide a system and method whereby oxygen can be supplied to the myocardium by means other than through the coronary arteries.

It is another object of the present invention to provide a system and method of supplying oxygen to the myocardium prior to the reopening of blocked heart vessels.

In addition, it is an object of the present invention to provide a system and method of supplying oxygen to the myocardium during critical periods of non-perfusion following an MI or during a PTCA procedure.

SUMMARY OF THE INVENTION

The objects above may be achieved according to the present invention by providing a system and method of supplying oxygenated carrier solutions directly to the at risk tissue by means other than through the coronary blood vessels. In particular, the objects of the present invention may be met by providing a catheter to infuse perfluorocarbon emulsions directly into the pericardial space; i.e. the space between the pericardium and the epicardial surface.

DETAILED DESCRIPTION OF THE INVENTION

The system and method of the present invention, makes it possible to oxygenate the heart for periods of 4 to 6 hours or more, through non-coronary routes. This is particularly important during periods when the heart cannot be adequately supplied with blood through the coronary blood vessels, such as in cases of MI and PTCA.

The system and method of the present invention also makes it possible to greatly reduce the risks and dangers associated with the development of ischemia. In particular, myocardial tissue can be reoxygenated following an MI much more rapidly by using the system and method of the present invention than is possible through the use of PTCA or thrombolytic agents. Further, the system and method of the present invention may be used in conjunction with PTCA or thrombolytic agent procedures, and can act to reoxygenate at risk tissue prior to such procedures taking effect. This is especially important in preventing the development of ischemia during a time consuming PTCA procedure, or a delayed dissolving action of a thrombolytic agent.

The system and method of the present invention can be employed in hospital coronary care units, emergency rooms, and even in emergency transport vehicles. This is important in preventing the development of ischemia during the critical period immediately following an MI.

Reduction of the early development of ischemia and avoiding the further development of ischemia during PTCA or thrombotic treatment, may drastically reduce the death rate attributable to MI's.

The use of preoxygenated carrier solutions in the system and method of the present invention avoids all of the disadvantages associated With supplying oxygen dissolved in saline to the pericardial space. In particular, the use of preoxygenated carrier solutions is relatively easy to control and monitor, acts to remove carbon dioxide from the tissue thus avoiding acidosis, and provides for higher concentrations of oxygen to be delivered to the cardiac tissue.

The system and method of the present invention comprises a catheter which is capable of supplying a preoxygenated carrier solution directly to the pericardial space. The catheter may be one of many known types or designs, but optimally includes a guiding catheter having two or more lumens, one of which can be used to provide a gentle vacuum, and the others of which act as channels for solution delivery, solution withdrawal, and for monitoring pericardial fluid pressure. The catheter also preferably includes means to assist in guiding the catheter to the proper location within a patient, such as through the use of ultrasound or fiber optic technology. In a further embodiment according to the present invention, the catheter includes three side by side lumens which are separated from each other over a length of about 3 to 6 cm from the tip. This design is advantageous in that having three lumens will permit the simultaneous infusion and withdrawal of pericardial perfusion solution and the recording of pericardial fluid pressure.

Preoxygenated carrier solution may be delivered through the delivery catheter from a standard administration means which is coupled to the catheter. Standard administration means can be any one of a syringe, an infusion bottle or bag, or other known means.

Suitable preoxygenated carrier solutions include normal physiological saline, 5% dextrose water, buffer solutions, electrolyte formulations such as Ringer's, etc., and emulsions of any aromatic or non-aromatic fluorocarbon. The preferred preoxygenated carrier solution is an emulsion of any aromatic or non-aromatic fluorocarbon. Further, any physiologically compatible solution that is capable of carrying an adequate volume of oxygen to the heart following subpericardial administration may be used. Preferably, the preoxygenated carrier solution is an emulsion of an emulsifying agent and at least one perfluorocarbon compound selected from the group consisting of perfluorodecalin, perfluorooctylbromide, perfluoromethyladamantane, perfluorobromoalkyl-ethers, Fluosol-DA 20%, perfluorohexylether, perfluorobutylethene, perfluoroisoproylhexylethene, perfluorobutylhexylethene, the general classes of perfluoroalkylethers, perfluoroalkylalkenes, perfluoroalkylarylethers, perfluoroalkylarylalkenes, perfluoroarylethers, and perfluoroarylalkenes, and other perfluoronated compounds which can be acceptably emulsified.

More preferably, the perfluorocarbon compound is at least one compound selected from the group consisting of Fluosol-DA 20%, perfluorooctylbromide, perfluorodecalin, perfluoromethyladamantane, perfluorobromoisobutyl-ether.

Suitable emulsifying agents can be either natural or synthetic or a suitable combination which optimizes particle size and performance. Preferably, the perfluorocarbon emulsion may be optimized by combining one or more aromatic or non-aromatic perfluorocarbon compounds with one or more natural or synthetic emulsifying agent.

The emulsions can be macroemulsions using standard egg yolk phospholipid as the emulsifying agent and having an average particle size of 50 to 3000 nanometers. Preferable, the macroemulsion has an average particle size of 100 to 400 nanometers. The emulsions may also be microemulsions using fluorinated surfactants as the emulsifying agent and having an average particle size of 10 to 100 nanometers. Preferably, the microemulsion has an average particle size of 30 to 60 nanometers.

When using a perfluorocarbon emulsion as the preoxygenated carrier solution, it is preferred to use perfluorocarbon compounds having a molecular weight of about 400 to 700. More preferably, the molecular weight of the perfluorocarbon compound should be in the rang of 450 to 550.

The amount of preoxygenated solution administered should be carefully controlled so as to avoid pericardial tamponade. Typical volumes for administration are in the range of 5 to 100 milliliters. In addition, it may be desirable to withdraw fluid at regular intervals and supply fresh emulsions to the pericardial space. Preferably, it is desirable to administer 10 to 2000 milliliters of a perfluorocarbon emulsion to the pericardial space over a time period of 30 minutes to 6 hours. Most preferably, an amount of 100 to 500 milliliters may be administered. It should be recognized that the volume of perfluorocarbon emulsion administered should be controlled to limit pericardial fluid pressure to less that 7 mm Hg. (Note Gonzalez et al; J. Am. Coll. Cardiol.; 17, pp 239-247, 1991.)

The solution administered to the pericardial space should be delivered in a temperature range of 20 to 42 degrees centigrade. Preferably, the solution should be a 37 degrees centigrade when delivered to the pericardial space.

As an example, the system and method according to the present invention can be practiced according to the following procedure. Initially, a percutaneous puncture of the thorax or other appropriate entrance location is carried out. The guiding catheter may then be advanced using a guidance system, such as ultrasound or fiber optics, until the guiding catheter reaches the surface of the pericardium. Using an empty syringe connected to the vacuum lumen of the guiding catheter, a slight vacuum may be pulled so as to separate the pericardium away from the heart to a distance of about one centimeter. The pericardium may then be punctured in a manner which avoids damage to the epicardial surface. Following the pericardial puncture, the delivery-withdrawal-pressure catheter (d-w-p catheter) is threaded through the channel lumen of the guiding catheter with the aid of a guidewire if needed. The d-w-p catheter is then advanced into the pericardial space and any guidewire is removed. The vacuum is then released and the guiding catheter is removed from the cardiac region.

The preoxygenated carrier solution such as perfluoromethyladamantane 50% W/W emulsified with egg yolk phospholipid, and prewarmed to body temperature (37° C.) is then administered into the pericardial space through the d-w-p catheter, by injection, infusion or other appropriate means. Administration of the preoxygenated carrier solution may be preceded by removal of some of the endogenous pericardial fluid, especially when such is present in an excessive amount. The amount of preoxygenated carrier solution administered should be carefully controlled so as to avoid pericardial tamponade. This can be accomplished by monitoring the amount administered by such means as 2D echocardiography ultrasound. Alternatively, the monitoring of increases in the right ventricular end diastolic pressure can alert one to the early signs of cardiac tamponade. In a preferred alternative, direct recording of the pericardial fluid pressure may be carried out through a lumen of the d-w-p catheter.

The preoxygenated carrier solution supplied to the pericardial space can then act to supply oxygen throughout the heart by transport via the lymphatics. In particular, by bringing the preoxygenated carrier solution into contact with the external cardiac surfaces, the lymph system acts to take up the solution and distributes the solution transmurally through the heart. The solution is then automatically released from the heart through the lymphatic drainage channels. Oxygenation by this means permits global oxygenation of the entire myocardium, and avoids the need of selective catheterization through blocked arteries. In addition, the oxygenation method according to the present invention provides for uptake and removal of carbon dioxide.

It is preferable to use perfluorocarbon emulsions as discussed above. Perfluorocarbon emulsions are generally of a size and lipophilicity that they can be readily taken up by the lymphatic channels. However, any physiologically compatible solution that is capable of carrying adequate volume of oxygen to the heart following subpericardial administration via the lymphatic channels may be used. Although isotonic solutions will be effective as oxygen carriers, hypotonic solutions may be more effective because the osmotic gradient would favor a more rapid uptake in the lymphatic fluids.

In a particular embodiment according to the present invention, the fluid supplied to the pericardial space is periodically withdrawn and fresh fluid is infused. This exchange of fluid may be accomplished using a standard syringe or manifold system. In a preferred alternative, an automated system which provides for continuous withdrawal and simultaneous replenishment of the fluid may be employed. The withdrawn fluid may be discarded or recycled through an oxygen-carbon dioxide gas exchanger so as to reoxygenate the fluid, and then reinfused. An appropriate gas exchanger would be the type used in heart-lung bypass surgery.

By withdrawing and replenishing fluid to the pericardial space, several advantages arise. In particular, the perfluorocarbon emulsion supplied to the pericardial space may have a much larger particle size which provides for optimum performance and minimum uptake into the cardiac lymphatics. The particle size range for the perfluorocarbon emulsion in this embodiment, may be from 50 to 50,000 nanometers, and preferably from 100 to 30,000 nanometers. Gas exchange between the perfluorocarbon emulsion and the lymph system is expected to take place at the interface between the lymph and the pericardial fluid.

It is expected that optimum performance may be achieved when part of the perfluorocarbon emulsion is absorbed into the lymph system and part is not. In such a case, less perfluorocarbon emulsion would be withdrawn from the pericardial space than had been added, the difference being the amount that had been absorbed and distributed to the body.

Therefore, a major advantage of partial removal and recycling of the perfluorocarbon emulsion from and to the pericardial space is the minimization of systemic uptake and distribution. A decreased uptake of the perfluorocarbon emulsion into the body, provides for a lower burden on the body, and therefore permits a prolongation of the period of oxygenation without overloading the body with perfluorocarbon emulsion.

Another advantage of periodic withdrawal and reinfusion, is that the perfluorocarbon fluid may be supplied to the pericardial space, in a neat condition; i.e. in an unemulsified condition. This allows for easier production of the perfluorocarbon fluid and also broadens the range of perfluorocarbon fluids that may be used.

Therefore, the present invention provides a system and method of supplying oxygen to the heart through means other than the coronary arteries. Further, the present invention provides a system and method of supplying oxygen to the myocardium prior to the reopening of blocked heart vessels. In addition, the present invention provides a system and method for supplying oxygen to the myocardium during critical periods of non-perfusion following an MI or during a PTCA procedure.

The present invention also has several other advantageous uses. In particular, once the delivery catheter is in place within the pericardial space, therapeutic agents and nutrients may be supplied to the heart. These agents or nutrients may be administered separately or in combination with the preoxygenated carrier solution in emulsion form. In a preferred embodiment, each of an oxygen carrying medium, a therapeutic drug carrying medium and a nutrient carrying medium may be supplied to the pericardial space simultanously.

The present invention may be used to deliver a wide variety of therapeutic agents, such as lidocaine, thrombolytic agents, anti-inflammatory drugs, and drugs which act to attenuate reperfusion damage to the heart. A wide variety of nutrients can also be delivered, such as glucose and fatty acids. These nutrients should be delivered at physiologically acceptable concentrations. Acceptable fatty acids can be chosen from C2 to C18 chain length fatty acids which are optimized in mixture and ratio.

The system and method of the present invention is also useful for application to tissues outside the cardiac area which require oxygenation. In particular, the system and method of the present invention can be used on any tissue which includes anatomical support structures and membranes which would allow administration as described above. For example, the system and method of the present invention may be used to oxygenate any tissue Which includes a covering sac or membrane which can be pulled away from the main surface of the tissue to form a space for the administration of the preoxygenated solution. A particular example is the subdural administration of preoxygenated carrier solutions, such as perfluorocarbon emulsions, to treat ischemia resulting from cerebral strokes. In this case, the perfluorocarbon emulsion would be infused under the dura into the cerebrospinal fluid over the surface or the brain.

The foregoing has been a description of certain preferred embodiments of the present invention, but is not intended to limit the invention in any way. Rather, many modifications, variations and changes in details may be made within the scope of the present invention.

What is claimed is:

1. A system for oxygenation of the heart, comprising
a guiding catheter;
a solution delivery catheter; and
means for supplying preoxygenated carrier solution through said delivery catheter;
wherein said guiding catheter provides means to guide said delivery catheter into the pericardial space between the pericardium and the epicardial surface of the heart;
wherein said delivery catheter is constructed so it may be threaded through said guiding catheter and includes means to contact the interior of the pericardial space;
wherein said means for supplying preoxygenated carrier solution comprises means for administering said carrier solution through said delivery catheter directly into the pericardial space, withdrawing said carrier solution from the pericardial space, and replenishing said carrier solution to the pericardial space.

2. A system according to claim 1, wherein said delivery catheter also includes means for withdrawing carrier solution from the pericardial space, and means for monitoring of pericardial fluid pressure.

3. A system according to claim 2, wherein said delivery catheter comprises a three lumen catheter, a first lumen for delivery of carrier solution to the pericardial space, a second lumen for withdrawing carrier solution from the pericardial space, and a third lumen for monitoring pericardial fluid pressure.

4. A system according to claim 3, wherein delivery and withdrawal of carrier solution, and monitoring of pericardial fluid pressure may be carried out simultaneously.

5. A system according to claim 3, wherein said guiding catheter comprises a two lumen catheter, wherein a first lumen is capable of providing a slight vacuum, and a second lumen is capable of guiding said three lumen catheter to the pericardial space.

6. A system according to claim 3, wherein said guiding catheter comprises a concentric dual lumen catheter, wherein an outer lumen is capable of providing a slight vacuum, and an inner lumen is capable of guiding said three lumen catheter to the pericardial space.

7. A system according to claim 1, wherein said carrier solution is periodically withdrawn from the pericardial space, and fresh carrier solution is infused to the pericardial space.

8. A system according to claim 7, wherein said carrier solution which has been withdrawn from the pericardial space, is reoxygenated by gas exchange in an oxygen-carbon dioxide gas exchanger, and then is reinfused to the pericardial space.

9. A system according to claim 1, wherein said carrier solution is continuously withdrawn from the pericardial space, and fresh carrier solution is simultaneously infused to the pericardial space.

10. A system according to claim 9, wherein said carrier solution which has been withdrawn from the pericardial space, is reoxygenated by gas exchange in an oxygen-carbon dioxide gas exchanger, and then is reinfused to the pericardial space.

11. A system according to claim 1, wherein said carrier solution is an emulsion of a emulsifying agent and at least one perfluorocarbon compound selected from the group consisting of perfluorodecalin, perfluorooctylbromide, perfluoromethyladamantane, perfluorobromoalkyl-ethers, Fluosol-DA 20%, perfluorohexylether, perfluorobutylethene, perfluoroisoproylhexylethene, perfluorobutylhexylethene, the general classes of perfluoroalkylethers, perfluoroalkylalkenes, perfluoroalkylarylethers, perfluoroalkylarylalkenes, perfluoroarylethers, and perfluoroarylalkenes, and other perfluoronated compounds which can be acceptably emulsified.

12. A system according to claim 11, wherein said perfluorocarbon compound is at least one compound selected from the group consisting of Fluosol-DA 20%, perfluorooctylbromide, perfluorodecalin, perfluoromethyladamantane, perfluorobromoisobutylether.

13. A system according to claim 11, wherein said emulsion has an average particle size of 50 to 50,000 nanometers.

14. A system according to claim 13, wherein said average particle size is 100 to 30,000 nanometers.

15. A system according to claim 1, wherein said carrier solution is at least one perfluorocarbon compound selected from the group consisting of perfluorodecalin, perfluorooctylbromide, perfluoromethyladamantane, perfluorobromoalkylethers, Fluosol-DA 20%, perfluorohexylether, perfluorobutylethene, perfluoroisoproylhexylethene, perfluorobutylhexylethene, the general classes of perfluoroalkylethers, perfluoroalkylalkenes, perfluoroalkylarylethers, perfluoroalkylarylalkenes, perfluoroarylethers, and perfluoroarylalkenes, and other perfluoronated compounds which can be acceptably emulsified.

16. A system according to claim 15, wherein said perfluorocarbon compound is at least one compound selected from the group consisting of Fluosol-DA 20%, perfluorooctylbromide, perfluorodecalin, perfluoromethyladamantane, perfluorobromoisobutylether.

17. A system according to claim 1, which may be used during a percutaneous transluminal coronary angioplasty, so as to prevent the development of ischemic tissue in the myocardium.

18. A system for oxygenation of body tissue, comprising
 a guiding catheter;
 a solution delivery catheter; and
 means for supplying preoxygenated carrier solution through said delivery catheter;
 wherein said guiding catheter provides means to guide said delivery catheter into a space between a covering membrane of the tissue and the surface of the tissue;
 wherein said delivery catheter is constructed so it may be threaded through said guiding catheter and includes means to contact the interior of said space;
 wherein said means for supplying preoxygenated carrier solution comprises means for administering said carrier solution through said delivery catheter directly into said space, withdrawing said carrier solution from said space, and replenishing said carrier solution to said space.

19. A system according to claim 18, wherein said tissue is the brain, and said system may be used to administer said carrier solution under the dura into the cerebrospinal fluid covering the surface of the brain.

20. A method of delivering a preoxygenated carrier solution to the heart of a patient, said method comprising;
 inserting a guiding catheter through the vasculature of the patient until said guiding catheter is in contact with the pericardium;
 providing a slight vacuum through said guiding catheter so as to separate the pericardium from the heart thereby forming a pericardial space between the pericardium and the epicardial surface of the heart;
 puncturing the pericardium;
 threading a delivery catheter through said guiding catheter until said delivery catheter is in contact with the interior of the pericardial space;
 delivering said carrier solution through said delivery catheter and into the pericardial space; and
 withdrawing carrier solution from and replenishing carrier solution to the pericardial space.

21. A method according to claim 20, wherein oxygen is provided to ischemic tissue in the myocardium following a myocardial infarction.

22. A method according to claim 20, wherein oxygen is provided to the myocardium during a percutaneous transluminal angioplasty procedure so as to prevent the development of ischemic tissue.

23. A method according to claim 20, wherein said delivery catheter also includes means for withdrawing carrier solution from the pericardial space, and means for monitoring of pericardial fluid pressure.

24. A method according to claim 23, wherein said delivery catheter comprises a three lumen catheter, a first lumen for delivery of carrier solution to the pericardial space, a second lumen for withdrawing carrier solution from the pericardial space, and a third lumen for monitoring pericardial fluid pressure.

25. A method according to claim 24, wherein delivery and withdrawal of carrier solution, and monitoring of pericardial fluid pressure may be carried out simultaneously 26. A method according to claim 23, wherein said guiding catheter comprises a two lumen catheter, wherein a first lumen is capable of providing a slight vacuum, and a second lumen is capable of guiding said three lumen catheter to the pericardial space.

27. A method according to claim 23, wherein said guiding catheter comprises a concentric dual lumen catheter, wherein an outer lumen is capable of providing a slight vacuum, and an inner lumen is capable of guiding said three lumen catheter to the pericardial space.

28. A method according to claim 20, wherein said carrier solution is periodically withdrawn from the pericardial space, and fresh carrier solution is infused to the pericardial space.

29. A method according to claim 28, wherein said carrier solution which has been withdrawn from the pericardial space, is reoxygenated by gas exchange in an oxygen-carbon dioxide gas exchanger, and then is reinfused to the pericardial space.

30. A method according to claim 20, wherein said carrier solution is continuously withdrawn from the pericardial space, and fresh carrier solution is simultaneously infused to the pericardial space.

31. A method according to claim 30, wherein said carrier solution which has been withdrawn from the pericardial space, is reoxygenated by gas exchange in an oxygen-carbon dioxide gas exchanger, and then is reinfused to the pericardial space.

32. A method according to claim 20, wherein said carrier solution is an emulsion of a emulsifying agent and at least one perfluorocarbon compound selected from the group consisting of perfluorodecalin, perfluorooctylbromide, perfluoromethyladamantane, perfluorobromoalkyl-ethers, Fluosol-DA 20%, perfluorohexylether, perfluorobutylethene, perfluoroisoproylhexylethene, perfluorobutylhexylethene, the general classes of perfluoroalkylethers, perfluoroalkylalkenes, perfluoroalkylarylethers, perfluoroalkylarylalkenes, perfluoroarylethers, and perfluoroarylalkenes, and other perfluoronated compounds which can be acceptably emulsified.

33. A method according to claim 32, wherein said perfluorocarbon compound is at least one compound selected from the group consisting of Fluosol-DA 20%, perfluorooctylbromide, perfluorodecalin, perfluoromethyladamantane, perfluorobromoisobutylether.

34. A method according to claim 32, wherein said emulsion has an average particle size of 50 to 50,000 nanometers.

35. A method according to claim 34, wherein said average particle size is 100 to 30,000 nanometers.

36. A method according to claim 20, wherein said carrier solution is at least one perfluorocarbon compound selected from the group consisting of perfluorodecalin, perfluorooctylbromide, perfluoromethyladamantane, perfluorobromoalkylethers, Fluosol-DA 20%, perfluorohexylether, perfluorobutylethene, perfluoroisoproylhexylethene, perfluorobutylhexylethene, the general classes of perfluoroalkylethers, perfluoroalkylalkenes, perfluoroalkylarylethers, perfluoroalkylarylalkenes, perfluoroarylethers, and perfluoroarylalkenes, and other perfluoronated compounds which can be acceptably emulsified.

37. A method according to claim 36, wherein said perfluorocarbon compound is at least one compound selected from the group consisting of Fluosol-DA 20%, perfluorooctylbromide, perfluorodecalin, perfluoromethyladamantane, perfluorobromoisobutylether.

38. A method of oxygenating body tissue of a patient, said method comprising;
    inserting a guiding catheter through the vasculature of the patient until said guiding catheter is in contact with a membrane surrounding said body tissue;
    providing a slight vacuum through said guiding catheter so as to separate the membrane from the tissue surface thereby forming a space between the membrane and the tissue surface;
    puncturing the membrane;
    threading a delivery catheter through said guiding catheter until said delivery catheter is in contact with the interior of said space;
    delivering said carrier solution through said delivery catheter and into said space; and withdrawing carrier solution from and replenishing carrier solution to said space.

39. A method according to claim 38, wherein said tissue is the brain, and said carrier solution is delivered under the dura into the cerebrospinal fluid covering the surface of the brain.

* * * * *